(12) United States Patent
Ory et al.

(10) Patent No.: US 6,264,702 B1
(45) Date of Patent: Jul. 24, 2001

(54) COMPOSITE PROSTHESIS FOR PREVENTING POST-SURGICAL ADHESIONS

(75) Inventors: Francois Régis Ory, Fontaines-Saint-Martin; Michel Therin, Lyons, both of (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/147,949

(22) PCT Filed: Jul. 22, 1998

(86) PCT No.: PCT/FR98/01624

§ 371 Date: Mar. 24, 1999

§ 102(e) Date: Mar. 24, 1999

(87) PCT Pub. No.: WO99/06079

PCT Pub. Date: Feb. 11, 1999

(30) Foreign Application Priority Data

Aug. 1, 1997 (FR) .................................................. 97 10102

(51) Int. Cl.⁷ ...................................................... A61F 2/02
(52) U.S. Cl. ..................................... 623/23.75; 623/23.76; 606/213; 602/49
(58) Field of Search ............................... 623/11.11, 23.75, 623/23.76; 606/213; 600/37; 602/49

(56) References Cited

U.S. PATENT DOCUMENTS

| | | | |
|---|---|---|---|
| 4,307,717 | * 12/1981 | Hymes et al. | 128/156 |
| 4,487,865 | * 12/1984 | Balazs et al. | 524/29 |
| 4,500,676 | * 2/1985 | Balazs et al. | 525/54.2 |
| 4,813,942 | * 3/1989 | Alvarez | 604/290 |
| 5,002,551 | * 3/1991 | Linsky et al. | 606/151 |
| 5,433,996 | * 7/1995 | Kranzler et al. | 600/37 |
| 5,593,441 | * 1/1997 | Lichtenstein et al. | 623/66 |
| 6,056,970 | 5/2000 | Greenawalt et al. | |

FOREIGN PATENT DOCUMENTS

| | | |
|---|---|---|
| 0 372 969 A1 | 6/1990 | (EP) . |
| 0705878 A2 | 4/1996 | (EP) . |
| WO 89/02445 | 3/1989 | (WO) . |
| WO 92/20349 | 11/1992 | (WO) . |
| WO 93/11805 | 6/1993 | (WO) . |
| WO 95/18638 | 7/1995 | (WO) . |
| WO 96/08277 | 3/1996 | (WO) . |

* cited by examiner

Primary Examiner—Paul B. Prebilic
(74) Attorney, Agent, or Firm—Oliff & Berridge, PLC

(57) ABSTRACT

Composite prosthesis, comprising a non-absorbable prosthetic fabric and at least one film made of a material which is absorbable in vivo, combined with one surface of the prosthetic fabric. In combination, the prosthetic fabric has a three-dimensional structure separating its two surfaces, at least one of which is open to all post-surgical cell colonization, and the film of absorbable material is linked at least superficially to the other surface of said fabric.

8 Claims, 2 Drawing Sheets

A  B  C  D  E

COMPOSITE PROSTHESIS FOR PREVENTING POST-SURGICAL ADHESIONS

The present invention concerns a composite prosthesis for preventing post-surgical adhesions, in particular in the field of visceral, parietal or neurological surgery. The invention will be described more particularly in relation to a composite prosthesis intended for use in parietal surgery, in the repair of eventrations or hernias.

Post-surgical adhesions include all non-anatomical fibrous connections accidentally induced by a surgical act during the normal process of cicatrization. They may occur in all surgical disciplines regardless of the operation in question. They are generally all the more severe, the greater the surgical trauma and the more affected the tissues which normally ensure the planes of division (interstitial connective tissue, the synovial membranes, the tendon sheaths, peritoneal and pleural serosa, etc.). Any surgical trauma to tissue is followed by a cascade of physiological events, the main times of which can be simplified as follows:

- time zero (t0): surgical trauma, capillary invasion;
- time zero plus a few minutes: coagulation, formation of fibrin network, release of chemotactic factors;
- time zero (t0) plus 12 to 48 hours: influx of leukocytes, predominantly polynuclears;
- time zero (t0) plus 24 hours to 5 days: influx of leukocytes, predominantly macrophages;
- time zero (t0) plus 4 to 8 days: influx of fibroblasts;
- time zero (t0) plus 5 to 14 days: conjunctive differentiation of the cicatricial reaction;
- time zero (t0) plus 15 to 180 days: cicatricial remodeling.

Although some of the exact mechanisms are still unknown, particularly as regards determination of the intensity of the reaction, it appears that the first few days are decisive since they condition the influx of fibroblasts responsible for the formation of adhesions.

For this reason, such post-surgical adhesions can provoke syndromes which can be classed principally as chronic pain, occlusive syndromes and female infertility. Furthermore, they increase very substantially the risks of making errors in follow-up surgery (myocardial or intestinal invasion during repeat thoracotomy or laparotomy), while prolonging the operating times, since the preliminary dissection can be very awkward in such cases.

One solution to this problem consists in interposing a physical barrier between the structures which one does not wish to see adhering. However, the desired barrier effect poses the problem of the intrinsic adhesive power of this barrier. The reason is that if the barrier is made of a non-absorbable material, it can itself be the source of adhesions over the course of time; and if it is absorbable, its absorption must be sufficiently non-inflammatory so as not to cause adhesions itself.

Several properties are therefore necessary if a material is to be able to reduce the risk of adhesions, namely, among others:

- the material must be substantially smooth and non-porous on at least one of its surfaces, so as not to offer space for cell recolonization;
- the surface of the material must limit the original cell adhesion.

Nevertheless, and in particular in visceral and parietal surgery, the barrier must also have a certain mechanical strength allowing it to fulfill its function as an element of surgical reconstruction. Generally speaking, the known prosthetic fabrics, particularly in the treatment of parietal insufficiencies, for example hernias and eventrations, afford an additional mechanical strength to the surgical reconstruction. Such fabrics are all the more effective and their local tolerance is all the better, the earlier and the more intimate their tissue integration. For this reason, the most effective of the known prosthetic fabrics for these indications are generally highly porous and are designed in such a way as to be integrated in the body as rapidly as possible. The term "porous" is intended to signify the characteristic according to which at least one of the surfaces of the fabric is rough, so as to present alveoli, distributed regularly or irregularly, and promoting all cell colonization. It is for this reason that upon contact with the viscera for example, these fabrics promote adhesion, which limits their use at the so-called preperitoneal or retroperitoneal sites. Now, in a number of cases, and more particularly in the case of multiple recurring eventrations, implantation strictly in the preperitoneal site is difficult, even impossible, on account of the existence of an extensive deficit of serosa.

There is therefore a requirement to make available a product which is able to solve the problem of preventing post-surgical adhesions, while at the same time offering a prosthetic reinforcement subject to cell recolonization and tissue integration, and which can be used, for example, to treat an eventration involving substantial peritoneal loss, or small eventrations, by laparoscopy, and hernias.

To this end, patent application WO-A-96/08277 describes a composite prosthesis comprising a prosthetic fabric, in this case an absorbable or non-absorbable lattice, and at least one film made of a crosslinked absorbable collagenous substance, in this case a collagen gel coagulated in the dry state, combined with one surface of the prosthetic fabric. The composite prosthesis thus formed finds an application in the treatment of eventrations and hernias and, according to the inventors, prevents post-operative adhesions because the collagenous membrane constitutes a zone of separation permitting release of any early post-operative adhesions that may develop.

The composite prosthesis according to document WO-A-96/08277 must be improved in respect of the necessary independence, once it is implanted, between, on the one hand, the phenomenon of cell colonization and tissue insertion, which must if possible be directed, and, on the other hand, the absorption of the film, which must be relatively rapid in vivo, in such a way as to limit the phenomena of inflammation.

Such is the object of the present invention.

According to the invention, in combination, on the one hand the prosthetic fabric has a three-dimensional structure separating its two surfaces, at least one of which is open to all post-surgical cell colonization, and, on the other hand, the film of absorbable material is linked at least superficially to the other surface of said fabric.

The term "open surface" is intended to signify that said surface includes alveoli having a certain depth according to the thickness of the three-dimensional fabric, these alveoli passing completely or incompletely through the thickness of the fabric, from one surface to the other. In the case of a complete passage of the alveoli, this will be referred to as an openwork prosthetic fabric or one having an openwork structure.

According to the invention, that surface of the absorbable film opposite the prosthetic fabric is preferably substantially smooth and non-porous.

The absorbable film is preferably made up of at least one polysaccharide derivative forming a hydrogel which is insoluble in aqueous medium.

By virtue of the invention, and in a controllable manner:
the prosthesis prevents immediate post-surgical cell colonization on the side including the absorbable film, which is absorbed during a period of time compatible with the tissue restoration, for example that of the peritoneum;
the prosthesis facilitates the immediate post-surgical cell colonization, on the surface including the fabric, open in such a way as to permit a rapid and mechanically effective integration thereof, in particular when it is used as a parietal or visceral reinforcement.

Preferably, but not exclusively, the prosthetic fabric comprises two opposite porous surfaces, connected to one another by connecting yarns, one of which is open to all post-surgical cell colonization, and the other of which is closed to said colonization by means of the film of absorbable material. For example, the weave of the prosthetic fabric determines, within the thickness of the latter, a multiplicity of alveoli or transverse channels, substantially parallel to one another, opening out on either side of said fabric on the two porous surfaces respectively, and of which the internal section is substantially free of any connecting yarn. This is therefore a flexible prosthetic fabric having a "honeycomb" structure.

Polysaccharide derivative is intended to signify both the polysaccharide considered in the pure state, as well as the latter when chemically modified, or mixed with other biocompatible products or adjuvants.

The polysaccharide is advantageously chosen from the group consisting of mucopolysaccharides, polyanionic polysaccharides, glycosaminoglycans, modified celluloses, and mixtures of these. The polysaccharide derivative is preferably chosen from the group consisting of a derivative of hyaluronic acid (HA) or its salts, a derivative of carboxymethylcellulose (CMC), a derivative of carboxymethylamylose (CMA), a derivative of chondroitin-6-sulfate, a derivative of dermatan sulfate, a derivative of heparin and a derivative of heparin sulfate, or a mixture of these.

Still more preferably, the polysaccharide derivative is a derivative of hyaluronic acid or one of its hyaluronic salts. Hyaluronic acid is a natural mucopolysaccharide which is present, inter alia, in the synovial fluid, in the walls of the blood vessels, the umbilical cord and in other connective tissues. Polysaccharide consists of residues of N-acetyl-D-glucosamine and D-glucuronic acid, connected by $\beta$1–3 glucuronide and $\beta$1–4 glucosaminide bonds, respectively, in such a way that the structural unit is designated -(1>4)-$\beta$-D-GlcA-(1>3)-$\beta$-D-GlcNAc. HA dissolves in water and forms a liquid of high viscosity. The molecular weight of HA isolated from natural sources is generally between $5\times10^4$ to [sic] $1\times10^7$ daltons. As used in the present application, the term "HA" comprises both hyaluronic acid and its hyaluronic salts, and includes, for example, sodium hyaluronate, potassium hyaluronate, magnesium hyaluronate and calcium hyaluronate.

The preferred HA derivative is insoluble in water, and biocompatible, and it can be obtained, for example, by reacting HA with a polyfunctional crosslinking agent, such as a polyfunctional epoxide. Generally speaking, the crosslinking or modifying procedures allowing an HA derivative to be obtained which is suitable for combination with the three-dimensional prosthetic fabric are well known per se and will not be described in detail here. These procedures are described in particular in the patent applications WO-A-89/02445, WO-A-92/00105 and WO-A-92/20349, the contents of these being incorporated in the present patent application as and when necessary.

The thickness of the absorbable film is advantageously less than the thickness of the prosthetic fabric, for example between 2% and 10% of the total thickness of the composite prosthesis, and preferably between about 30 $\mu$m and 100 $\mu$m, and more preferably about 50 $\mu$m to 75 $\mu$m.

The absorbable film which forms part of the composite prosthesis of the invention is biocompatible, non-toxic, and is absorbed rapidly in vivo. The absorbable material used can equally well be of animal origin, human origin or synthetic.

In a preferred embodiment, the absorbable film is linked at least superficially to the prosthetic fabric, directly or indirectly, and is preferably linked directly by capillary absorption, within a certain thickness of the material, in the constituent fibers of the prosthetic fabric.

Still more preferably, the absorbable film is linked directly by capillary absorption of the absorbable material in the constituent fibers of the prosthetic fabric over a depth of less than 750 $\mu$m, measured from the outer surface of the film.

According to the invention, a composite prosthesis comprises two surfaces which are different in their appearances and functions, namely one surface which is porous or open on one side, in order to accommodate and direct the post-surgical cell colonization, and the other surface is closed for tissue separation without adhesion.

The absorbable film is preferably continuous, smooth and non-porous, entirely covering the prosthetic fabric, and more preferably projects beyond the latter in such a way as to protect the prosthesis from visceral contacts, the overshoot being from 5 to 10 millimeters for example.

The absorbable film is intimately linked to the fabric by surface penetration so as not to constitute a plane of division or delamination, while at the same time maintaining the porosity of the fabric open on the other surface.

The absorbable film is preferably also flexible, in particular in the hydrated state, in such a way as to preserve the manageability of the prosthesis, and its possible use by the celioscopic route.

Once rehydrated, the film restores to the prosthetic fabric its initial mechanical properties (flexibility and elasticity) without fragmenting, and without making the fixation of the prosthesis more difficult. It is additionally transparent, cannot be delaminated and cannot stick when being put into position. Its rapid absorption ensures protection against the initial adhesive phenomena, that is to say in the first week following surgery, or in other words during the period of time necessary for the tissue integration of the opposite surface. Upon its absorption, its weakly inflammatory and/or immunogenic character does not disturb the tissue colonization on the opposite side of said film.

The present invention will be better understood from the detailed description of a preferred embodiment, given by way of example, with reference being made to the attached drawing, in which.

Figure 1:
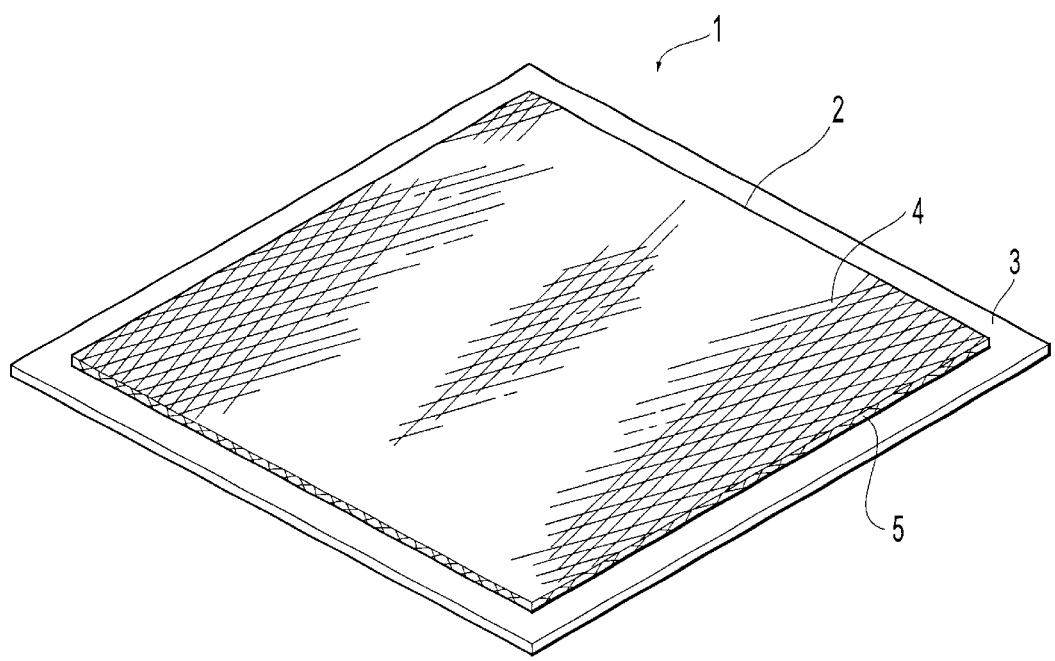
FIG. 1 represents diagrammatically a composite prosthesis according to the present invention.

Referring usefully to FIG. 1, a composite prosthesis according to the present invention is designated in a general manner by reference number 1. The prosthesis includes a prosthetic fabric 2 having two surfaces 4 and 5, one of which is covered with a film 3 of polysaccharide derivative. The prosthetic fabric 2 has an openwork three-dimensional structure and thus a certain thickness which separates the surface 4 from the surface 5. This fabric can preferably be a raschel knit formed on a double needle-bed. The spacing of the two needle beds and the delivery speeds of the yarns allow a finished fabric to be obtained in three dimensions (three-dimensional structure), with a thickness of between 1 to [sic] 3 mm, and for example of about 1.8 mm, for a weight of about 90 g/m². The final characteristics are given independently of the knitting by the choice of basic material employed, for example multiyarn polyester PES 50 dtex, the temperature, and the thermosetting time. Apart from the spinning, the yarn and the fabric do not receive any other treatment (no oiling or washing). Such a fabric has, in accordance with standard NFG 07119, a tensile strength of between about 18 daN and about 30 daN, and a stretch at break of between about 25% to [sic] 37%, in warp, and a tensile strength of between about 9 daN and 15 daN, and a stretch at break of between 60% to [sic] 88%, in weft.

Figure 2:
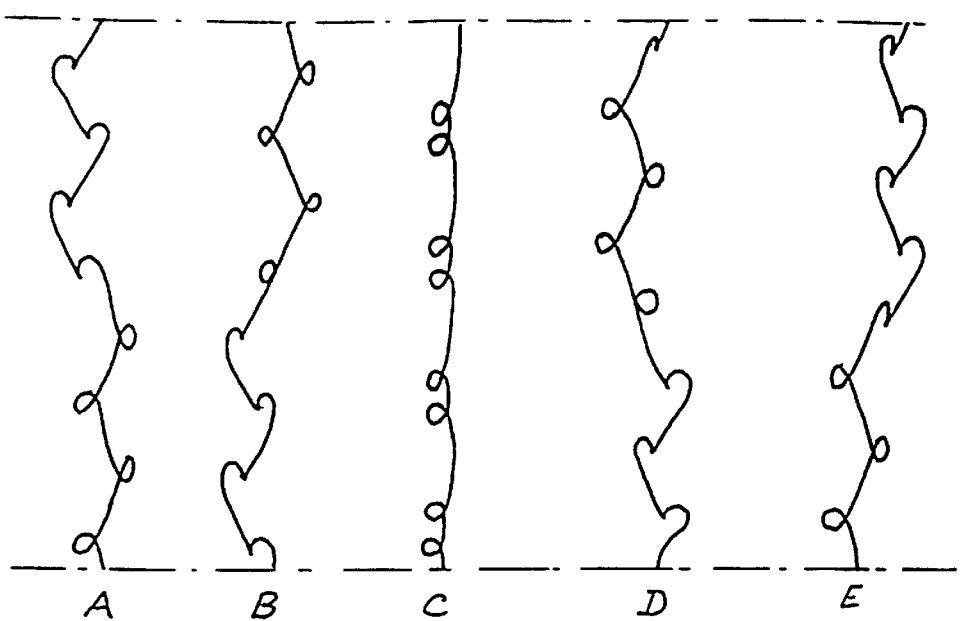
FIG. 2 represents a diagrammatic sketch of the knitted weave of a prosthetic fabric belonging to a composite prosthesis according to the present invention.

Such a composite fabric can be formed by warp knitting of five layers of yarns, and in accordance with the diagrammatic sketch in FIG. 2. In this figure, each layer of yarns is identified by a letter, ranging from A to E, the sketch itself using a knitting description system which is entirely familiar and comprehensible to the person skilled in the art, and which will not be described in detail here. According to FIG. 2, the preferred prosthetic fabric according to the present invention is, as has already been described, made up of two independent porous surfaces. In the given example, these two surfaces are themselves made up of two layers of yarns, labeled A, B and D, E respectively, the layers A, B giving a surface with tear-shaped openings, in order to accommodate and direct the post-surgical cell colonization, and the layers D, E giving a surface with hexagonal openings which will be closed by the film of collagenous substance. The prosthetic fabric can be knitted on a double-rib raschel loom. In this case, all the bars corresponding to the yarns A, B and D, E are threaded one full/one empty. The layer of connecting yarns is represented by reference C and is threaded full. The different layers A–E of yarns are all knitted at the same time. Thus, the connecting yarns are distributed along the peripheral edges of the openings of each surface and extend substantially perpendicular from one surface to the other surface, preventing connecting yarns from occupying too great a volume of the transverse channels which are formed. The final fabric can then be stabilized simply by heating it at a temperature of between about 170° C. and about 220° C.

It follows from the above description that the yarns making up the three-dimensional fabric are of a non-absorbable but biocompatible nature, hence different than that of the absorbable material of the film.

A composite prosthesis combining a prosthetic fabric of three-dimensional openwork structure, as obtained above, with a film of polysaccharide derivative can be produced in the following way.

The solution containing the polysaccharide derivative is spread uniformly over a plane and hydrophobic inert support to form a resulting film made up of two thin superposed layers. To do this, a first thin layer of the solution is initially applied. After this first thin layer has gelled by means of cooling, a second thin layer of the same solution is applied to its surface.

The prosthetic fabric of three-dimensional openwork structure, having a thickness of the order of 1.8 mm, is applied via its surface with hexagonal openings on the second thin layer, before gelling, so that the fabric anchors in the polysaccharide derivative during the drying of the film. After the reaction, the composite prosthesis is separated from the hydrophobic inert support.

It should be noted that the film of polysaccharide derivative can ascend by capillarity in the fibers, this effect being partly responsible for the high resistance to delamination of the film from the prosthetic fabric. Finally, the film is continuous, and no synthetic fiber originating from the prosthetic fabric appears at its surface. Furthermore, the film has a thickness of the order of 50 µm to 75 µm, but, by capillarity in the fibers of the prosthetic fabric, can reach as far as a thickness of about 750 µm.

What is claimed is:

1. A composite prosthesis comprising:

a non in vivo-absorbable prosthetic fabric having a weave or knit comprising a three-dimensional structure separating two opposite surfaces, said opposite surfaces connected to one another by connecting yarn, one of said surfaces being porous and open to post-surgical cell colonization, and the other of said surfaces being closed to said colonization;

one film made of at least one polysaccharide derivative hydrogel, which is insoluble in an aqueous medium but absorbable in vivo;

said film having a thickness less than a thickness of the prosthetic fabric; and said film being linked directly to constituent yarns of the prosthetic fabric by capillary absorption of the polysaccharide derivative in a depth of said prosthetic fabric and into said constituent yarns.

2. A composite prosthesis according to claim 1, wherein the polysaccharide derivative is selected from the group consisting of mucopolysaccharides, polyanionic polysaccharides, glycosaminoglycans, modified celluloses, and mixtures thereof.

3. A composite prosthesis according to claim 1, wherein the polysaccharide derivative is selected from the group consisting of a derivative of hyaluronic acid or one of its hyaluronic salts, a derivative of carboxymethylcellulose, a derivative of carboxymethylamylose, a derivative of chondroitin-6-sulfate, a derivative of dermatan sulfate, a derivative of heparin, a derivative of heparin sulfate, and mixtures thereof.

4. A composite prosthesis according to claims 1, wherein the polysaccharide derivative is a derivative of hyaluronic acid, or one of its hyaluronic salts.

5. A composite prosthesis according to claim 1, wherein said other surface is closed to post-surgical cell colonization into the prosthetic fabric by said film.

6. A composite prosthesis according to claim 5, wherein the weave or knit of the prosthetic fabric comprises within its thickness a multiplicity of alveoli or transverse channels having an internal section free of any connecting yarn, said alveoli or channels being substantially parallel to one another and opening out on either side of said fabric on the two surfaces respectively.

7. A composite prosthesis according to claim 5, wherein the prosthetic fabric has a honeycomb structure.

8. A composite prosthesis according to claim 5, wherein the fabric has an open work structure such as obtained by weaving or knitting on a double rib raschel boom with at least five yarns threaded at the same time, one full and one empty.

* * * * *